United States Patent [19]

Anzeveno et al.

[11] Patent Number: 5,093,501

[45] Date of Patent: Mar. 3, 1992

[54] INTERMEDIATES IN A PROCESS FOR THE PREPARATION OF CASTANOSPERMINE

[75] Inventors: Peter B. Anzeveno, Zionsville; Paul T. Angell; Laura J. Creemer, both of Indianapolis, all of Ind.

[73] Assignee: Merrell Dow Pharmaceuticals Inc., Cincinnati, Ohio

[21] Appl. No.: 712,780

[22] Filed: Jun. 10, 1991

Related U.S. Application Data

[62] Division of Ser. No. 492,507, Mar. 12, 1990, Pat. No. 5,066,807.

[51] Int. Cl.$^5$ .................. C07D 405/04; C07D 307/92; C07D 317/70
[52] U.S. Cl. .................................... 548/526; 549/299; 549/433; 549/435
[58] Field of Search ...................... 549/299, 433, 435; 548/526

[56] References Cited

PUBLICATIONS

CA 108:6355q, The Synthesis of polyhydroxylated . . . dihydroxyproline, Bashyal et al., Tetrahedron (1987).
CA 113:97939a, Efficient synthesis . . . deoxynojirimycin, Anzeveno et al., Tetrahedron Letter (1990).
CA 114:164582q, An efficient, . . . castanospermine, Anzeveno et al., Tetrahedron Letter (1990).

Primary Examiner—Mary C. Lee
Assistant Examiner—Joseph K. McKane
Attorney, Agent, or Firm—John J. Kolano

[57] ABSTRACT

Castanospermine is prepared by starting from 5-(t-BOC)amino-5-deoxy-1,2-O-isopropylidene-α-D-glucuronolactone. Two additional carbons are added to the starting material using ethyl acetate and a strong base and the resulting cyclic hemiketal is subjected to a series of reductions, with intervening removal of protecting groups, to give the castanospermine. A substituted hydroxypyrrolidinone and a substituted hydroxypyrrolidine serve as intermediates in the process.

3 Claims, No Drawings

INTERMEDIATES IN A PROCESS FOR THE PREPARATION OF CASTANOSPERMINE

The present application is a division of application Ser. No. 07/492,507, filed Mar. 12, 1990, now U.S. Pat. No. 5,066,807.

BACKGROUND OF THE INVENTION

Castanospermine is a naturally occurring indolizidine alkaloid that has been found to inhibit enzymatic glycoside hydrolysis. Anti-cancer, anti-viral and anti-AIDS activities have also been reported for the compound. In addition, esters and glycosyl derivatives of castanospermine have also been described in the literature (see European Patent Application 0 297 534) and such compounds have been described as active as inhibitors of digestive enzymes and useful in treating diabetes.

Castanospermine was initially obtained by extraction from its natural sources and can be obtained in kilogram quantities in that way. However, the process is expensive and would be limited by the availability of the plant sources. More recently, castanospermine has been obtained synthetically by a variety of different procedures such as those described by Bernotas et al., *Tetrahedron Letters*, 25, 165 (1984); Setoi et al., *Tetrahedron Letters*, 26, 4617 (1985); Hamana et al., *J. Org. Chem.*, 52, 5492 (1987); and Reymond et al., *Tetrahedron Letters*, 30, 705 (1989). The various procedures are either quite lengthy and low-yielding and/or non-specific in that they require the separation of significant amounts of intermediate co-products with undesired stereochemistry or the procedures suffer from other disadvantages.

Thus, for example, although Reymond et al. may emphasize that their methology is "highly stereoselective", the yields in a number of steps are poor. In addition, although Hamana et al. describes his process as "the most efficient to date," it actually makes use of an ozonolysis step which would limit its value in any large scale syntheses.

SUMMARY OF THE INVENTION

The present invention thus relates to a new process for the synthesis of castanospermine which is both short and highly stereoselective. More specifically, the present invention relates to a new process for the preparation of castanospermine starting from 5-(t-BOC)amino-5-deoxy-1,2-O-isopropylidene-α-D-glucuronolactone. The term t-BOC or BOC, as used above and in the present application, refers to the group t-butoxycarbonyl.

The process of the present invention can be illustrated structurally as follows:

Specifically, the present invention relates to a process for converting 5-(t-BOC)amino-5-deoxy-1,2-O-isopropylidene-α-D-glucuronolactone to castanospermine which comprises (a) reacting 5-(t-BOC)amino-5-deoxy-1,2-O-isopropylidene-α-D-glucuronolactone (I) with ethyl acetate and a strong base in an inert solvent at low temperature whereby the ethyl acetate adds across the carbonyl group of the lactone to give the corresponding cyclic hemiketal of a β-keto ester (II); (b) hydrogenating the hemiketal catalytically under pressure over a platinum catalyst in ethyl acetate to reduce the β-keto function and give the β-hydroxy ester (III); (c) treating the β-hydroxy ester with formic acid in an inert solvent with cooling to remove the protecting group from the amine followed by basification and internal cyclization of the resulting amine to give lactam (IV); (d) reducing the lactam with an aluminum hydride reducing agent to give the corresponding pyrrolidine (V); and (e) treating the pyrrolidine first with trifluoroacetic acid with cooling and then hydrogenating over platinum catalyst under pressure to give castanospermine (VI).

In step (a), the strong base removes an α-hydrogen from the ethyl acetate and the resulting anion adds to the carbon atom of the lactone carbonyl. Lithium diisopropylamine is a preferred strong base for the reaction and tetrahydrofuran is a preferred solvent. The reaction is carried out with cooling in a dry ice/acetone bath so that the temperature is about −78° C.

In the hydrogenation in step (b), two epimeric β-hydroxy esters can be formed and the use of platinum oxide in ethyl acetate at a pressure of about three atmospheres favors the formation, by a ratio of 7:2 with respect to the other isomer, of the hydroxy isomer required for the synthesis of castanospermine. When other solvents are used, poorer ratios of the desired isomer are obtained while other catalysts give no reaction. Hydride reducing agents favor the formation of the undesired hydroxy isomer. Although a mixture of isomers is obtained even under the most favorable conditions, the two isomers obtained can be separated by chromatography and the desired isomer can still be isolated in good yield (about 79%).

Hydrolysis of Compound III to remove the t-butoxycarbonyl protecting group from the amino-group is carried out using formic acid because other common hydrolyzing agents work poorly. The hydrolysis actually gives the formate salt of the resulting amine and a solution of this salt is basified to convert it to the free amine. Use of a basic ion exchange resin, in the form of a column, is preferred for this basification. With the formation of the free amine, internal cyclization with the ester function takes place to give the corresponding γ-lactam (IV).

Reduction of the lactam (IV) to the corresponding cyclic amine (pyrrolidine) (V) is accomplished by the use of an aluminum hydride reducing agent in a inert solvent. Lithium aluminum hydride in an ether solvent such as tetrahydrofuran is preferred for this conversion.

The ketal protecting group is removed from the cyclic amine (V) by treatment with an acid with cooling. Trifluoroacetic acid at about 0° C. is preferred for this purpose. The resulting product is a cyclic hemiacetal which, in the open hydroxy aldehyde form, can recyclize on to the pyrrolidine nitrogen to give a second ring (a piperidine ring). The resulting unsaturated bicyclic compound is then hydrogenated catalytically under pressure using a catalyst such as platinum on carbon, with water as the solvent, at a pressure of about three atmospheres. This procedure gives castanospermine (VI) which is identical with natural castanospermine.

The 5-(t-BOC)amino-5-deoxy-1,2-O-isopropylidene-α-D-glucuronolactone used as the starting material in the above process can be obtained from 1,2-O-isopropylidene-5-oxo-α-D-glucuronolactone by the following series of reactions:

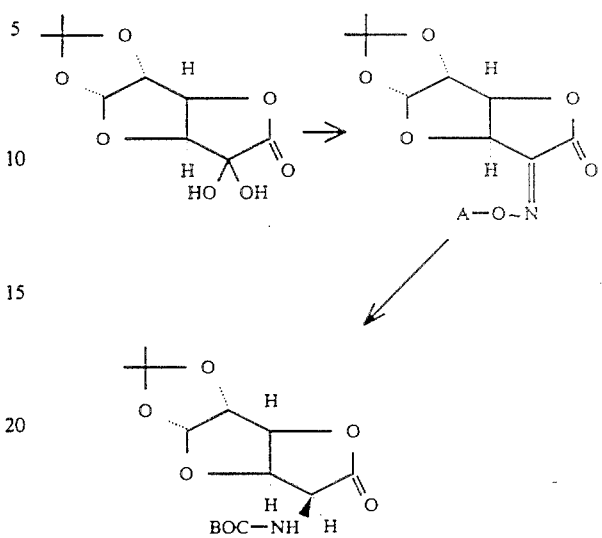

In this process, the 5-oxo compound (hydrated form) is reacted with an O-substituted hydroxylamine, wherein A is the O-substituent, to give the corresponding 5-oxime which is then hydrogenated catalytically in the presence of t-BOC-anhydride to give the desired compound. The group A is preferably benzyl or trimethylsilyl.

The following examples are presented to illustrate the present invention but they should not be construed as limiting it in any way.

DETAILED DESCRIPTION OF THE INVENTION

Example 1

1,2-O-Isopropylidene-5-oxo-α-D-glucuronolactone Hydrate

To a cold (−70° C.) solution of dimethyl sulfoxide (10.7 g, 0.14 mol) in methylene chloride (200 mL) a solution of oxalyl chloride (8.0 mL, 0.09 mol) in methylene chloride (50 mL) was added dropwise at such a rate to maintain the reaction temperature below −55° C. After stirring for 0.5 hour below −70° C., a solution of 1,2-O-isopropylidene-α-D-glucuronolactone (10.0 g, 0.046 mol) in methylene chloride (100 mL) was added dropwise while again maintaining the reaction temperature below −55° C. The addition required 10 min. After stirring at −70° C. for 3 h, triethylamine (18.0 mL, 0.13 mol) was added dropwise, again maintaining the temperature below −55° C. This addition required 5-10 min. After an additional 15 min, the cooling bath was removed, water (2.0 mL) added, and the reaction mixture allowed to warm to ambient temperature. Ethyl acetate (350 mL) was added and the resulting suspension poured through silica gel (250 mL) and eluted with ethyl acetate (500 mL). Concentration of the eluate left crude product (10.0 g, 94%). Recrystallization of a sample from ethyl acetate hexane (1:1) gave pure 1,2-O-isopropylidene-5-oxo-α-D-glucuronolactone hydrate as colorless needles: mp 145°-148° C.; 1H NMR (acetone-$d_6$)δ 1.41 (s,3, $CH_3$), 1.57(s,3,$CH_3$), 4.62 (d,1,J=3.1 Hz,H-3), 4.91 (d,1,J=3.7 Hz,H-2), 4.98 (d,1,J=3.1 Hz,H-4), 5.26 (s,1,OH), 5.50 (s,1,OH), 6.03 (d,1,J=3.7

Hz,H- 1); mass spectrum, m/z (rel intensity) 215 (MH+-H₂O, 100), 185 (15), 157 (12).

Example 2A 1,2-O-Isopropylidene-5-oxo-α-D-glucuronolactone O-Benzyloxime

To a suspension of 1,2-O-isopropylidene-5-oxo-α-D-glucuronolactone hydrate (1.85 g, 7.9 mmol) in benzene (40 mL), O-benzylhydroxylamine hydrochloride (1.28 g, 7.9 mmol) was added and the resulting mixture refluxed for 3 hours. (Complete dissolution of the hydroxylamine and starting material occurred during this period.) The solution was then cooled and the solvent removed. Chromatographic purification of the residual viscous oil over silica gel (100 mL) with ethyl acetate-hexane (1:3) as eluent gave 2.51 g (99%) of 1,2-O-isopropylidene-5-oxo-α-D-glucuronolactone O-benzyloxime as a colorless viscous oil which slowly solidified on standing. NMR analysis showed a single oxime isomer present. An analytical sample was obtained as colorless prisms by recrystallization from benzene-hexane (1:1): mp 83°-85° C.;¹H NMR (CDCl₃) δ 1.36(s,3,CH₃), 1.52 (s,3, CH₃), 4.86 (d,1,J=3.5 Hz,H-2), 4.91 (d,1,J=4.4 Hz,H-3), 5.42 ('AB' subspectra, 2, J$_{AB}$=13.7 Hz,CH₂), 5.51 (d,1,J=4.4 Hz,H-4), 6.00 (d,1,J=3.5 Hz,H-1), 7.37 (m,5,C₆H₅); ¹³C NMR(CDCl₃) δ 26.66, 27.34, 60.02, 72.22, 79.60, 83.15, 83.23, 107.07, 113.71, 128.54, 128.62, 128.74, 128.83, 135.46, 144.52, 162.96; mass spectrum, m/z (rel intensity) 320 (MH+, 100), 262 (15), 91 (90).

Example 2B 1,2-O-Isopropylidene-5-oxo-α-D-glucuronolactone O-(trimethylsilyl)oxime A well-stirred, nitrogen-blanketed mixture of 1,2-O-isopropylidene-5-oxo-α-D-glucuronolactone hydrate (0.45 g, 1.9 mmol) and O-(trimethylsilyl)hydroxylamine (0.24 g, 2.3 mmol) in benzene (30 mL) was heated to reflux, during which time a homogeneous solution was obtained, and refluxed for 2 h. The reaction was cooled to ambient temperature and the solvent evaporated at reduced pressure. The residual thick oil was dissolved in ethyl acetate (~35 mL) and the solution filtered through a celite pad to remove any insoluble material. The filtrate was concentrated, leaving 0.6 g (~100%) of crude 1,2-O-isopropylidene-5-oxo-α-D-glucuronolactone O-(trimethylsilyl)oxime as an off-white, amorphous solid. This was an ~3:2 mixture of oxime stereoisomers by ¹H NMR analysis, and was not further characterized. The crude oxime was used without further purification in subsequent reactions: ¹H NMR (DMSO-d6)δ 6.03 (d,1,J=4.0 Hz) 5.42 (d,1,J=4.3 Hz) 5.05 (d,1,J=4.3 Hz), 4.90 (d,1,J=4.0 Hz), 1.44 (s,1), 1.29 (s,1), 0.00 (s,9); mass spectrum (CI/CH₄) m/z (rel intensity) 302 (MH+,4) 258 (12), 230 (100), 172 (40), 95 (60).

Example 3A 5-(t-BOC)amino-5-deoxy-1,2-O-isopropylidene-α-D-glucuronolactone from O-Benzyloxime To a solution of 1,2-O-isopropylidene-5-oxo-α-D-glucuronolactone O-benzyloxime (3.16 g, 9.9 mmol) and (BOC)₂O (2.38 g, 10.9 mmol) in ethyl acetate (20 mL) was added 0.5 g of 10% Pd/C and the resulting suspension stirred for 0.5 h under nitrogen. The catalyst was removed by filtration and washed with ethyl acetate (10 mL). Fresh Pd/C (0.9 g) was added to the filtrate, and the mixture hydrogenated on a Parr apparatus at 3 atmospheres for 60 h. The catalyst was filtered, washed with ethyl acetate (15 mL) and the filtrate concentrated. Chromatography of the residue over silica gel (80 mL) with ethyl acetate-hexane (1:3) as eluent yielded 1.85 g (59%) of 5-(t-BOC)amino-5-deoxy-1,2-O-isopropylidene-α-D-glucuronolactone. An analytical sample was obtained by recrystallization from ethyl acetate-hexane (1:1) as colorless needles: mp 157°-159° C.; ¹H NMR (CDCl₃) δ 1.35 (s,3, CH₃), 1.46 (s,9, C₄H₉), 1.52 (s,3,CH₃), 4.78 (dd,1,J=8.8,4.2 Hz,H-5), 4.82 (d,1,J=3.7 Hz,H-2), 4.84 (d,1,J=3.0 Hz,H-3), 4.95 (dd,1,J=4.2,3.0 Hz,H-4), 5.10 (d,1,J=8.8 Hz,NH), 5.93 (d,1,J=3.7 Hz,H-1); mass spectrum, m/z(rel intensity) 316 (MH+,5), 288 (20), 260 (100), 216 (40).

Example 3B 5-(t-BOC)amino-5-deoxy-1,2-O-isopropylidene-α-D-glucuronolactone (I) from O-(trimethylsilyl)oxime When the procedure of Example 3A was repeated using 1.2-O-isopropylidene-5-oxo-α-D-glucuronolactone O-(Trimethylsilyl)oxime in place of the O-benzyloxime, 5-(t-BOC)amino-5-deoxy-1,2-O-isopropylidene-α-D-glucuronolactone was obtained in an average yield of about 60%.

Example 4

Ethyl 5,7-dideoxy-5-[[(t-butoxy)carbonyl]amino]-1,2-O-(1-methylethylidene)-α-D-gluco-6-octulo-1,4:6,3-difuranuronate To a well-stirred, nitrogen-blanketed solution of diisopropylamine (7.7 mL, 55.0 mmol) in anhydrous tetrahydrofuran, cooled to −78° C. (dry ice/acetone), a 1.6M solution of n-butyllithium in hexane (34.4 mL, 55.0 mmol) was added dropwise during 5 minutes. The resulting solution was stirred for 20 min at −78° C., then ethyl acetate (5.5 mL, 56.2 mmol) was added dropwise during 10–15 min while maintaining the reaction temperature below −70° C. After 20 min, a solution of 5-(t-BOC)amino-5-deoxy-1,2-O-iso-propylidene-α-D-glucuronolactone (I) (5.3 g, 16.8 mmol) in tetrahydrofuran (50 mL) was added dropwise while again maintaining the reaction temperature below −70° C. This addition required about 20 min. The reaction solution was stirred an additional 2 h at −78° C., then allowed to warm to −10° C. and poured onto a stirred mixture of 1N hydrochloric acid (100 mL) and ice (~100 g). This mixture was extracted with ethyl acetate (3×100 mL) and the combined extracts were washed with sat. sodium bicarbonate (100 mL) and brine (100 mL), then dried (MgSO₄) and concentrated at reduced pressure. The oily residue was flash-chromatographed over silica gel (100 mL) using 3% acetone in methylene chloride as eluent. Pure ethyl 5,7-dideoxy-5-[[(t-butoxy)carbonyl]amino]-1,2-O-(1-methylethylidene)-α-D-gluco-6-octulo-1,4:6,3-difuranuronate (II) (6.6 g, 97%) was obtained as a colorless oil which by ¹H NMR analysis was a single isomer, identified by NOE experiments as that in which the N-BOC and acetate moieties were trans: [α]$_D^{25}$= +10.7° (c 2.3, CHCl₃); ¹H NMR (CDCl₃) δ 6.03 (d,1, J=3.7Hz, H-1), 5.57 (s,1,OH), 5.38 (d,1, J=9.5 Hz, NH), 4.88 (dd, 1, J=5.4, 5.4 Hz, H-4), 4.68 (d, 1, J=3.7 Hz, H-2) 4.67 (d, 1, J=5.4Hz, H-3), 4.21 (q, 2,J=7.2 Hz, CH₂CH₃), 3.84 (dd, 1, J=9.5, 5.4 Hz, H-5), 2.82 (d, 1,J=16.3 Hz, H-7), 2.59 (d, 1,J=16.3 Hz, H-7'), 1.46 (s,3, CH₃), 1.45 (s,9, t-C₄H₉), 1.34 (s,3, CH₃), 1.29 (t,3, J=7.2 Hz, CH₂CH₃); ¹³C NMR (CDCl₃) δ 13.9, 27.1, 27.6, 28.2, 40.8, 59.1, 61.3, 79.8, 80.8, 84.0, 86.7, 101.9, 107.1, 113.0, 155.3, 172.3; mass spectrum, m/z (rel intensity) 404 (MH$^+$, 80), 386 (MH$^+$-H$_2$O, 30), 330 (MH$^+$-C$_3$H$_6$O$_2$, 100), 286 (40), 214 (25).

Example 5

Preparation of Ethyl 5,7-dideoxy-5-[[(t-butoxy)carbonyl]amino]-1,2-O-(1-methylethylidene)-L-glycero-α-D-glucooctofuranuronate (III)

A solution of 10.0 g (24.8 mmol) of ketol-ester II in ethyl acetate (150 mL) was hydrogenated at three atmospheres over PtO$_2$ (4.0 g) catalyst for 20 h on a Parr apparatus. The catalyst was filtered off through a bed of Celite and washed with ethyl acetate (50 mL). The combined filtrate was concentrated at reduced pressure, leaving 10.0 g (100%) of an oily mixture of two isomeric amino-diols (a and b) which by hplc analysis [Waters Hypersil ODS (C18, 5μ) column (250 mm×4.6 mm); CH$_3$CN(60)/H$_2$O (40) eluent; 1.5 mL/min flow rate; about 100 atmospheres pressure; retention time a (the desired isomer)=3.4 min. [b=2.9 min] was a 7:2 mixture of the two, with a predominating. This mixture was flash chromatographed over 750 mL of silica gel using 4% acetone in methylene chloride as eluent. Twenty five×125 mL fractions were collected after a forerun of 500 mL. Fractions 10–17 contained pure a (5.0 g), fractions 18–23 contained a mixture of a and b (3.5 g) and fractions 24 and 25 contained b. Rechromatography of the material from fractions 18–23 afforded an additional 2.9 g of ethyl 5,7-dideoxy-5-[[(t-butoxy)carbonyl]amino]-1,2-O-(1-methylethylidene)-L-glycero-α-D-gluco-octofuranuronate (a, III) for a yield of 79%. The isolated a slowly crystallized on standing. An analytical sample was obtained as colorless prisms from (1:4) ether-petroleum ether, bp. 35°–60° C.: mp 102°–104° C.; [α]$_D^{25}$=+21.8° (c 2.3, CHCl$_3$);1H NMR (CDCl$_3$) δ 5.93 (d, 1, J=3.7 Hz, H-1), 5.32 (d, 1, J=9.1 Hz, NH), 4.85 (br s, 1, OH), 4.56 (d, 1, J=3.7 Hz, H-2), 4.56 (m, 1, H-6), 4.17 (q, 2, J=7.2 Hz CH$_2$CH$_3$), 4.13 (m, 1,H-4), 4.05 (d, 1, J=2.2 Hz, H-3), 3.61 (dd, 1, J=9.4, 9.1 Hz, H-5), 3.44 (br s, 1, OH), 2.67 (dd, 1, J=16.2, 9.5 Hz, H-7), 2.44 (dd, 1, J=16.2, 3.6 Hz, H-7'), 1.50 (s, 3, CH$_3$), 1.45 (s, 9, t-C$_4$H$_9$), 1.32 (s, 3, CH$_3$), 1.27 (t,3, J=7.2Hz, CH$_2$CH$_3$); $^{13}$C NMR (CDCl$_3$) δ 14.2, 26.2, 26.8, 28.2, 38.6, 51.9, 60.9, 65.4, 74.1, 80.1, 81.1, 84.5, 105.1, 111.6, 157.6, 172.6; mass spectrum, m/z(rel intensity) 406 (MH$^+$, 32), 350 (MH$^+$-C$_4$H$_8$, 35), 334 (MH$^+$-C$_4$H$_8$O, 25), 306 (MH$^+$-C$_5$H$_9$O$_2$, 100), 292 (13), 100 (46).

Example 6

[3aR-[3aα,5α(4S*,5R*),6α,6aα]]-4-Hydroxy-5-(tetrahydro-6-hydroxy-2,2-dimethylfuro[2,3-d]-1,3-dioxol-5-yl)-2pyrrolidinone (IV)

To a cold (0°–5° C.) well-stirred, nitrogen-blanketed solution of BOC-amino-diol III (13.3 g, 32.7 mmol) in methylene chloride (135 mL), 98% formic acid (400 mL) was added dropwise during 10 minutes. This solution was stirred at 0°–5° C. for 1 h then at ambient temperature for 6 h and finally, concentrated to dryness in vacuo at 30° C., leaving 12.3 g of thick, viscous oil. This was dissolved in water (50 mL) and adsorbed onto a column of 1L of Dowex 1×2 basic ion exchange resin (prewashed with 1.5L of 1N aqueous sodium hydroxide and then H$_2$O to neutrality (~5.0L)) and eluted with water. After a forerun of 500 mL, five×125 mL fractions, followed by ten×300 mL fractions were collected. Crystalline [3aR-[3aα,5α(4S*,5R*),6α,6aα]]-4-Hydroxy-5-(tetrahydro-6-hydroxy-2,2-dimethylfuro[2,3-d]-1,3-dioxol-5-yl)-2-pyrrolidinone (IV), 6.3 g (73% for the two steps) was obtained from fractions 13–36. An analytical sample was obtained as fine colorless needles by recrystallization from methanol: mp 263°–265° C.; [α]$_D^{25}$=−39.3° (c 0.67, H$_2$O); $^1$H NMR (DMSO-d$_6$) δ 7.34 (br s, 1, NH), 5.82 (d, 1, J=3.7 Hz, H-1), 5.10 (d, 1, J=4.7 Hz, 3-OH), 5.00 (d, 1, J=4.9 Hz, 6-OH), 4.40 (d, 1, J=3.7 Hz, H-2), 4.23 (ddd, 1, J=5.4, 4.2, 1.0 Hz, H-6), 4.18 (dd, 1, J=9.6, 2.7 Hz, H-4), 4.11 (dd, 1, J=4.7, 2.7 Hz, H-3), 3.60 (dd, 1, J=9.6, 4.2 Hz, H-5), 2.48 (dd, 1, J=16.6, 5.4 Hz, H-7),1.95 (dd, 1, J=16.6, 1.0 Hz, H-7'), 1.37 (s,3,CH$_3$), 1.24 (s,3, CH$_3$); $^{13}$C NMR (DMSO-d$_6$)δ 26.3, 26.8, 41.3, 56.9, 66.5, 73.3, 77.4, 84.9, 104.5, 110.6, 175.8; mass spectrum, m/z (rel intensity) 260 (MH$^+$, 100), 202 (MH$^+$-C$_3$H$_6$O, 23).

Example 7

[3aR-[3aα,5α(2R*,3S*),6α,6aα]]-2-(Tetrahydro-6-hydroxy-2,2-dimethylfuro[2,3-d]-1,3-dioxol-5-yl)-3-pyrrolidinol (V)

To a well-stirred, nitrogen-blanketed suspension of lithium aluminum hydride (2.3 g, 60.0 mmol) in anhydrous tetrahydrofuran (150 mL), lactam IV (3.0 g, 11.5 mmol) was added in portions during 3–5 min at 25° C. Caution: and H$_2$ evolution. This mixture was refluxed for 20 h then cooled to 0°–5° C. and the reaction quenched by the careful, sequential addition of water (2.5 mL), 1N NaOH (2.5 mL) and water 7.5 mL). This mixture was stirred at about 5° C. for 20 min then filtered through a pad of Celite. The collected aluminate salts were washed with tetrahydrofuran (200 mL) and the combined filtrate and wash was concentrated to dryness at reduced pressure, leaving 1.7 g of [3aR-[3aα,-5α(2R*,3S*),6α,6aα]]-2-(Tetrahydro-6-hydroxy-2,2-dimethylfuro[2,3-d]-1,3-dioxol-5-yl)-3-pyrrolidinol (V) as a white powder. The collected aluminate salts were refluxed with 100 mL of tetrahydrofuran-water (9:1) for 45 min. The salts were filtered, washed with tetrahydrofuran (50 mL) and the combined filtrate evaporated to dryness, leaving 0.5 g more of V for a total yield of 77%. An analytical sample was obtained as fine, colorless needles by recrystallization from methanol mp 223°–225° C. (dec); [α]$_D^{25}$=−5.0 (c 0.32, H$_2$O); $^1$H NMR (CDCl$_3$) δ 5.92 (d, 1, J=3.8 Hz, H-1), 4.55 (d, 1, J=3.8 Hz, H-2), 4.40 (ddd, J=5.3, 3.6, 1.6 Hz, H-6), 4.25 (d, 1, J=2.6 Hz, H-3), 4.13 (dd, 1, J=7.8, 2.6 Hz, H-4), 3.50 (m, 3, OH, NH), 3.18 (ddd, 1, J-11.2, 7.8, 7.6 Hz, H-8'), 3.12 (dd, 1, J=7.8, 3.6 Hz, H-5), 2.86 (ddd, 1, J=11.2, 9.5, 5.1 Hz, H-8), 2.05 (dddd, J=13.8, 9.5, 7.6, 5.3 Hz, H-7'), 1.86 (dddd, J=13.8, 7.8, 5.1, 1.6 Hz, H-7), 1.50 (s, 3, CH$_3$), 1.32 (s, 3, CH$_3$); $^{13}$C NMR δ 26.1, 26.6, 35.4, 43.2, 61.6, 70.6, 75.6, 77.9, 85.3, 103.8, 110.1; mass spectrum, m/z(rel intensity) 246 (MH$^+$,100), 188 (MH$^+$-C$_3$H$_6$O, 52).

Example 8

(+)-Castanospermine

A solution of [3aR-[3aα,5α(2R*,3S*),6α,6aα]]-2-(Tetrahydro-6-hydroxy-2,2-dimethylfuro[2,3-d]-1,3-dioxol-5-yl)-3-pyrrolidinol (V) (0.5 g, 2.0 mmol) in trifluoroacetic-water (9:1) (25 mL) was stirred, under nitrogen, at ambient temperature for 20 h. The purple solution was then concentrated in vacuo (40° C.) leaving a thick syrup which was dissolved in deionized water (25 mL). This solution was basified to a pH of about 9.0 by the addition of 1N aqueous sodium hydroxide (5.5 mL) and hydrogenated at 3.4 atmospheres over 5% Pt on carbon (0.3 g) on a Parr apparatus for 16 h. The mixture was filtered through a celite pad and the collected catalyst washed with water (2×20 mL). The combined filtrate was adsorbed on a column of Dowex 50 W-X8 (H+) ion exchange resin (10 mL) (prewashed with 200 mL of water) and eluted first with deionized water (200 mL) and then with 1N ammonium hydroxide solution (twenty×20 mL fractions were collected). (+)-Castanospermine (VI), 0.23 g (61%) was obtained from fractions 1-15. An analytical sample was obtained as colorless prisms by recrystallization from 90% ethanol: mp 210°-212° C. dec. [lit. 212°-215° C. dec]; $[\alpha]_D^{25} = 81.4°$ (c 1.0, H$_2$O) [lit. $[\alpha]D^{25} = +79.7°$ (C 0.93, H$_2$O)]; $^1$H NMR (D$_2$O) δ 4.42 (ddd, 1, J=7.0, 4.5, 2.1Hz, H-1), 3.62 (ddd, 1, J=10.6, 9.4, 5.1 Hz, H-6), 3.60 (dd, 1, J=9.8, 9.0 Hz, H-8), 3.32 (dd, 1, J=9.8, 9.0 Hz, H-7) 3.18 (dd, 1, J=10.8, 5.1 Hz, H-5), 3.08 (ddd, 1, J=9.0, 8.8, 8.8 Hz, H-3), 2.34 (dddd, 1, J=13.9, 9.0, 7.0, 2.2 Hz, H-2), 2.22 (ddd, 1, J=9.3, 9.0, 8.8 Hz, H-3'), 2.06 (dd, 1, J=10.8, 10.6 Hz, H-5'), 2.02 (dd, 1, J=9.8, 4.5Hz, H-8a), 1.71(dddd, 1, J=13.9, 9.3, 8.8, 2.1 Hz, H-2'); $^{13}$C NMR (D$_2$O) δ 35.6, 54.5, 58.3, 71.9, 72.5, 73.0, 74.3, 81.9; mass spectrum, m/z(rel intensity) 190 (MH+, 50), 172 (MH+-H$_2$O, 100).

What is claimed is:

1. A compound selected from ethyl 5,7-dideoxy-5-[[(t-butoxy)carbonyl]amino]-1,2-O-(1-methylethylidene)-α-D-gluco-6-octulo-1,4:6,3-difuranuronate, ethyl 5,7-dideoxy-5-[[(t-butoxy)carbonyl]amino]-1,2-O-(1-methylethylidene)-L-glycero-α-D-gluco-octofuranuronate, [3aR-[3aα,5α(4S*,5R*),6α,6aα]]4-hydroxy-5-(tetrahydro-6-hydroxy-2,2-dimethylfuro[2,3-d]-1,3-dioxol-5-yl)-2-pyrrolidinone, and [3aR-[3aα,5α(2R*,3S*),6α,6aα]]-2-(tetrahydro-6-hydroxy-2,2-dimethylfuro[2,3-d]-1,3-dioxol-5-yl)-3-pyrrolidinol.

2. A compound according to claim 1 which is [3aR-[3aα,5α(4S*,5R*),6α,6aα]]-4-hydroxy-5-(tetrahydro-6-hydroxy-2,2-dimethylfuro[2,3-d]-1,3-dioxol-5-yl)-2-pyrrolidinone.

3. A compound according to claim 1 which is [3aR[-3aα,5α(2R*,3S*),6α,6aα]]-2-(tetrahydro-6-hydroxy-2,2-dimethylfuro[2,3-d]-1,3-dioxol-5-yl)-3-pyrrolidinol.

* * * * *

UNITED STATES PATENT AND TRADEMARK OFFICE
CERTIFICATE OF CORRECTION

PATENT NO. : 5,093,501

DATED : March 3, 1992

INVENTOR(S) : Peter B. Anzeveno, Paul T. Angell and Laura J. Creemer

It is certified that error appears in the above-identified patent and that said Letters Patent is hereby corrected as shown below:

```
   Column 8, line 27, "Caution: and" should read -- Caution:
foaming and --.
```

Signed and Sealed this

Thirty-first Day of August, 1993

Attest:

BRUCE LEHMAN

Attesting Officer

Commissioner of Patents and Trademarks